June 23, 1953 R. H. F. MANSKE Plant Pat. 1,198
DICENTRA PLANT
Filed Dec. 8, 1951
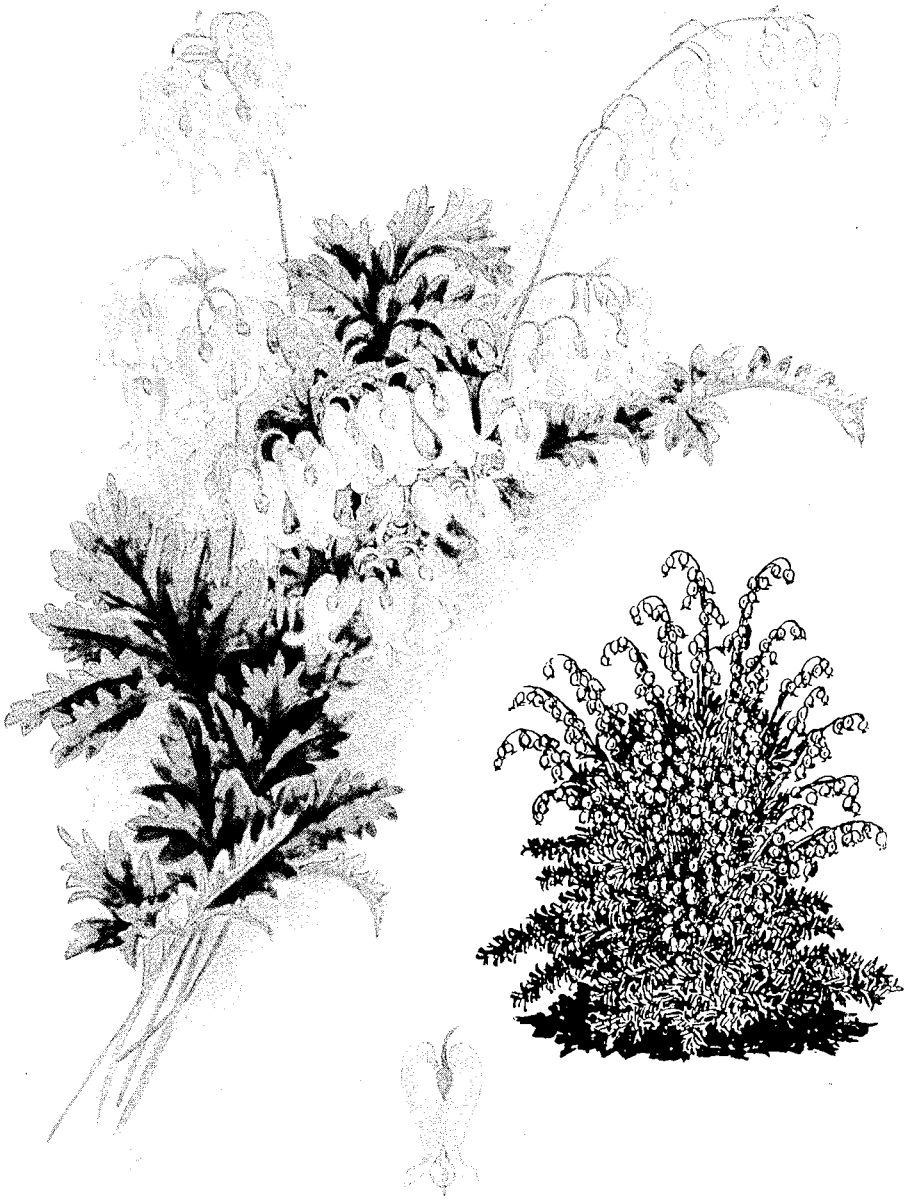
WITNESS
Addison E. Avery
INVENTOR
Richard H. F. Manske,
by: John A. Lionard,
his ATTY.

Patented June 23, 1953

Plant Pat. 1,198

UNITED STATES PATENT OFFICE 1,198

DICENTRA PLANT

Richard H. F. Manske, Guelph, Ontario, Canada, assignor to John J. Grullemans, Cleveland, Ohio Application December 8, 1951, Serial No. 260,684

1 Claim. (Cl. 47—60)

This invention relates to a new and distinct variety of Dicentra plant.

The new variety is illustrated in the drawings, in which:

The large colored view at the left illustrates typical leaf and flower stalks of the plant bearing leaves and blossoms;

The black and white sketch at the right shows a part of the plant as a whole, illustrating the relatively upright growth of the stalks; and The colored view at the bottom is a side elevation of a single blossom of the plant.

The new variety was developed as follows:

A *Dicentra oregana* Eastwood plant, as a seed parent, was crossed with a *Dicentra eximia* (Ker) Torrey plant, as a pollen parent. Neither of said plants is patented. Seeds from this crossing were planted in beds in close proximity to each other and allowed to cross pollinate freely. Seeds from this mass planting were again planted in beds in close proximity and exposed to open pollination. The new variety was selected from seeds produced in this second mass planting.

The new variety was selected from this second natural crossing.

The new variety was first developed by me in Ottawa, Ontario, Canada, and was asexually reproduced by me in Guelph, Ontario, Canada, by root division.

The root of the new variety of Dicentra plant is fibrous and of the usual size. However, the root has exceptional resistance to disease, and good resistance to wetness, drought and pests. Its winter resistance is very good as is indicated by the fact that it has withstood winter temperatures as low as 40° below zero, Fahrenheit, when unprotected. The root grows best in rich humous soil in partially shaded locations.

The exposed portion of the plant is herbaceous and bushy and larger than either its ancestor *Dicentra oregana* or its ancestor *Dicentra eximia*. It grows to a height of about 18 inches to 24 inches with a spread of about 24 inches. As a whole it is symmetrical and of flattened globular shape. The exposed portion of the plant is of vigorous growth. Its resistance to drought and wetness is good. None of the specimens has been damaged by insects or other pests.

The exposed plant structure does best when the plant is grown in partially shaded locations in well drained rich humous soil. However, very lightly shaded locations or even sunny locations are preferred over deep shade.

The stalks are stiff and are somewhat more upright than usual. They support the foliage, blooms, and fruits well. The more upright growth of the flower stalks is particularly noticeable, these stalks being recurrent only at their upper extremities, as indicated in the black and white sketch which, it is to be noted, shows only a portion of a full clump. The flower stalks are larger than usual for Dicentra plants.

The color of the new growth is glaucous green, that of the old growth being pale to dark green. The color is generally uniform for each stalk.

The leaf and flower stalks are basal, grouped and divergent, and range from about 12 inches to 18 inches in length. They have a smooth surface texture.

The foliage is dense yet lacy. The leaves are compound and abundant.

The top surfaces of the leaves are green, ranging in color from Maerz and Paul chart Pl. 22–K–7 to 22–A–7. The under surfaces of the leaves are generally a green comparable to Maerz and Paul chart Pl. 21–A–6, though sometimes they are slightly reddish. The leaves are either of the usual size or somewhat larger than usual and are of medium thickness. They are compound pinnate with serrated margins and acute apices. Their upper and lower surfaces are smooth. Their persistency on the plant is excellent.

The leaf stems average about 10 inches to 12 inches in length and are of medium strength. Their surface texture is smooth.

The new variety blooms well in the temperate zone, preferring a geographical range from the State of Virginia, U. S. A., north to Ontario and Quebec, Canada. The best blooms are produced in wet cold blooming seasons with the plant growing in moist, well drained, rich, sandy loam. The plant is essentially a cooler climate plant and does best in growth and blooming in short daylight.

The new variety generally has two blooming periods, the first beginning in the spring, earlier than that of the *Dicentra eximia*, and lasting well into July, and the second beginning in the fall and continuing until cold weather. The plant blooms as abundantly in the fall blooming season as in spring blooming season.

Cutting of the flower stalks in bloom does not effect the blooming characteristics of the remaining stalks.

The blooms, or bangles, are borne pendant on or near the terminals of the flower stalks on pedicels of medium strength and 1 inch to 1½ inches long. They are larger than the blooms of their *Dicentra oregana* or *Dicentra eximia* ancestors, being about double the usual size of bloom of the common bleeding heart plant. Their permanence on the plant is excellent and is fair even on the cut stalks. The shape of the blooms is substantially as illustrated in the drawings.

The color of the bloom is a magenta shading into pink, comparable to Maerz and Paul chart plates 41–J–1 and 41–H–1.

The genital organs and fruit of the plant are usual, the seeds being small and reniform.

The new variety regularly bears an abundance of large blooms and adapts itself well to various latitudes, climates and soils.

In general, the new variety is much more vigorous vegetatively than any of its known ancestors.

The new variety is characterized by its outstanding hardiness and vigorousness, its extreme floriferousness, its long blooming period, or periods, the large size and wide range of good colors of its flowers, its longer flower stalks which are basal in all cases, its hardiness and resistance to drought and cold, its more generally upright growth, and its propensity to bloom both in the spring and fall.

Having shown and described my new variety of Dicentra plant, I claim:

The new variety of Dicentra plant herein shown and described, characterized by its outstanding hardiness and vigorousness, its extreme floriferousness, its long blooming period, or periods, the large size and wide range of good colors of its flowers; its longer flower stalks which are basal in all cases, its hardiness and resistance to drought and cold, its more generaly upright growth, and its propensity to bloom both in the spring and fall.

RICHARD H. F. MANSKE.

No references cited.